United States Patent
Hill et al.

(10) Patent No.: US 10,539,580 B2
(45) Date of Patent: Jan. 21, 2020

(54) SOLID PHASE MULTI-ANALYTE ASSAY

(75) Inventors: Virginia Hill, Los Angeles, CA (US); Mohammad Atefi, Los Angeles, CA (US); Michael I. Schaffer, Los Angeles, CA (US)

(73) Assignee: Psychemedics Corporation, Acton, MA (US)

( * ) Notice: Subject to any disclaimer, the term of this patent is extended or adjusted under 35 U.S.C. 154(b) by 0 days.

(21) Appl. No.: 12/990,451

(22) PCT Filed: Apr. 29, 2009

(86) PCT No.: PCT/US2009/042061
§ 371 (c)(1),
(2), (4) Date: Jan. 18, 2011

(87) PCT Pub. No.: WO2009/134855
PCT Pub. Date: Nov. 5, 2009

(65) Prior Publication Data
US 2011/0118138 A1 May 19, 2011

Related U.S. Application Data

(60) Provisional application No. 61/048,892, filed on Apr. 29, 2008.

(51) Int. Cl.
*G01N 33/94* (2006.01)
(52) U.S. Cl.
CPC ......... *G01N 33/94* (2013.01); *G01N 33/9486* (2013.01); *Y10S 435/96* (2013.01)

(58) Field of Classification Search
None
See application file for complete search history.

(56) References Cited

U.S. PATENT DOCUMENTS

| | | | |
|---|---|---|---|
| 4,956,467 | A | 9/1990 | Hinman et al. |
| 5,324,642 | A | 6/1994 | Baumgartner |
| 5,340,748 | A | 8/1994 | Baugher et al. |
| 5,466,579 | A | 11/1995 | Baumgartner |
| 6,022,693 | A | 2/2000 | Baumgartner |
| 6,350,582 | B1 | 2/2002 | Baumgartner |
| 6,509,196 | B1 * | 1/2003 | Brooks et al. ............ 436/514 |

(Continued)

FOREIGN PATENT DOCUMENTS

| | | |
|---|---|---|
| CN | 1673745 | 9/2005 |
| CN | 1777684 | 5/2006 |

(Continued)

OTHER PUBLICATIONS

Nielen (2006) J Chrom 830: 126-134.*

(Continued)

*Primary Examiner* — Melanie Brown
*Assistant Examiner* — Richard Moerschell
(74) *Attorney, Agent, or Firm* — Fish & Richardson P.C.

(57) ABSTRACT

Compositions and methods for detecting the presence and/or amount of one or more analytes, including analytes such as drugs of abuse, are provided. The compositions include two or more analytes associated with a solid phase, e.g., a particle or a multiwell plate. The compositions and methods also allow the simultaneous, tandem, or serial determination of the presence and/or amount of two or more analytes of interest in a sample.

18 Claims, 3 Drawing Sheets

Simultaneous Assay

(56) References Cited

U.S. PATENT DOCUMENTS

| | | | |
|---|---|---|---|
| 6,582,924 | B1 | 6/2003 | Baumgartner |
| 6,949,344 | B1 | 9/2005 | Baumgartner |
| 7,083,925 | B2 | 8/2006 | Schnabel et al. |
| 7,252,961 | B2 | 8/2007 | Neuenhoger et al. |
| 7,297,554 | B2 | 11/2007 | Chung et al. |
| 7,618,591 | B2 | 11/2009 | Slowey et al. |
| 7,629,129 | B1 | 12/2009 | Sekowski et al. |
| 8,084,215 | B2 | 12/2011 | Hill et al. |
| 8,329,417 | B2 | 12/2012 | Hill et al. |
| 8,435,747 | B2 | 5/2013 | Hill et al. |
| 2003/0017479 | A1* | 1/2003 | Kaplan ............... A01K 67/0336 435/6.16 |
| 2004/0241776 | A1 | 12/2004 | Geister et al. |
| 2005/0106641 | A1* | 5/2005 | Kauvar ............... G01N 15/0625 435/7.21 |
| 2005/0148023 | A1* | 7/2005 | Thadhani ............. G01N 33/689 435/7.1 |
| 2005/0148041 | A1* | 7/2005 | Hirama ................ C07D 263/58 435/7.93 |
| 2006/0003396 | A1* | 1/2006 | Spivey et al. ................ 435/7.92 |
| 2008/0026403 | A1* | 1/2008 | Jacobson ............... C12Q 1/485 435/7.1 |
| 2008/0176340 | A1* | 7/2008 | Soldo et al. .................. 436/518 |
| 2009/0269791 | A1 | 10/2009 | Hill et al. |

FOREIGN PATENT DOCUMENTS

| | | |
|---|---|---|
| CN | 1885038 | 12/2006 |
| CN | 1977166 | 6/2007 |
| EP | 0 458 594 | 6/1996 |
| JP | 06-503424 | 4/1994 |
| WO | WO93/003368 | 2/1993 |
| WO | WO96/19500 | 6/1996 |
| WO | WO1999030160 A1 | 6/1999 |
| WO | WO1999042838 A1 | 8/1999 |
| WO | WO2001084157 A2 | 11/2001 |
| WO | WO2006078618 A2 | 7/2006 |
| WO | WO09/134855 | 11/2009 |

OTHER PUBLICATIONS

Law (2005) Immunoassay, a practical guide.*
Crowther (2001) The ELISA Guidebook.*
Mendoza (1999) BioTechniques 27: 778-788.*
Du et al (2005) Biomed Microdev 7: 143-146.*
Baumgartner (1979) J of Nucl Med 20:748-752.*
Maggio, eds Enzyme Immunoassay (1980) CRC Press, Boca Raton, FL, Maggio, Chapter 3, p. 54-70.*
Xu (1992) Clin Chem 38: 2038-2043, (Year: 1992).*
International Preliminary Report On Patentability; Baharlou, Simin; dated Nov. 2, 2010; World Intellectual Property Organization (WIPO) (International Bureau of); PCT/US2009/042061; 9 pages.
Cheze et al; Pharmaceuticals in Hair; Analytical and Practical Aspects of Drug Testing in Hair; 2007; pp. 163-185; CRC Press.
Du et al; Parallel detection and quantification using nine immonoassays in a protein microarray for drug from serum samples; Biomedical Microdevices; 2005; pp. 7(2):143-146.
Du et al; Preparation of steroid antibodies and parallel detection of multianabolic steroid abuse with conjugated hapten microarray; Analytical Chemistry; 2004; pp. 76(20):6166-6171.
Hartmann et al; Selective DNA attachment of micro- and nanoscale particles to substrates; J. Mater. Res.; 2002; pp. 17(2):473-478.
Jurado; Hair Analysis for Cocaine; Analytical and Practical Aspects of Drug Testing in Hair; 2007; pp. 95-125; CRC Press.
International Search Report and Written Opinion; Pellegrini, Paolo; dated Sep. 15, 2009; World Intellectual Property Organization (WIPO) (International Bureau of); PCT/US2009/042061; 13 pages.
Yegles et al; Opiods Testing in Hair; Analytical and Practical Aspects of Drug Testing in Hair; 2007; pp. 73-94; CRC Press.
Authorized Officer Monika Langerova, International Search Report/ Written Opinion in PCT/US09/42056 dated Jul. 10, 2009, 10 pages.
Authorized Officer Monika Langerova, International Search Report/ Written Opinion in PCT/US09/42061 dated Sep. 15, 2009, 15 pages.
"Benzodiazepines" [online]. U.S. Drug Enforcement Administration, [retrieved on Jun. 27, 2008]. Retrieved from the Internet: <URL: http://www.usdoj.gov/dea/concern/benzodiazepines.html>, 2 pages.
"Drug Intelligence Brief, Club Drugs: An Update, Sep. 2001" [online]. U.S. Drug Enforcement Administration, 2001, [retrieved on Jun. 27, 2008]. Retrieved from the Internet (Wayback machine): http://web.archive.org/web/20011120064344/http://www.usdoj.gov/dea/pubs/intel/01026/index.html, 1 page.
"Enzyme" Wikipedia.org, printed on Aug. 3, 2011 [http://en.wikipedia.org/wiki/Enzyme], 26 pages.
"Morphine and 6-Monoacetylmorphine in Hair of Heroin Users: Use of Invalid Extraction Procedures Generates Erroneous Conclusions," *J. of Anal. Toxicology*, Letter to the Editor, 29 (Jan./Feb. 2005).
"Protease" Wikipedia.org, printed on Aug. 3, 2011 [http://en.wikipedia.org/wiki/Protease], 4 pages.
"Proteolysis" Wikipedia.org, printed on Aug. 3, 2011 [http://en.wikipedia.org/wiki/Proteolysis], 2 pages.
Ahrens et al., "Detection of morphine and monoacetylmorphine (MAM) in human hair," *Fresenius' Journal of Analytical Chemistry*, 1992, 344(12):559-560.
Antignac et al., "Mult-residue extraction—purification procedure for corticosteroids in biological samples for efficient control of their misuse in livestock production," *Journal of Chromatography B*, 757: 11-19 (2001).
Baumgartner, "Radioimmunoassay of Hair for Determining Opiate Abuse Histories," *J. Nucl. Med.*, 1979, 20:749-752.
Cleland et al., "A Specific and Sensitive Assay for Disulfides," *J. of Bio. Chem*, 243(4): 716-719 (1968).
Cleland, "Dithiothreitol, a New Protective Reagent for SH Groups," *Biochemistry*, 3(4): 480-482 (1963).
Dunnett et al., "Retrospective Detection and Deposition Profiles of Potentiated Sulphonamides in Equine Hair by Liquid Chromatography," *Chromatographia*, 59: S69-S78 (2004).
Dunnett et al., "Trace element, toxin and drug elimination in hair with particular reference to the horse," *Res. in Vet. Science*, 75: 89-101 (2003).
Gaillard et al., "Gas chromatographic-tandem mass spectrometric determination of anabolic steroids and their esters in hair: Application in doping control and meat quality control," *J. of Chroma B.*, 735(2): 189-205 (1999).
Getz et al., "A Comparison between the Sulfhydryl Reductants Tris(2-carboxyethyl)phosphine and Dithiothreitol for Use in Protein Biochemistry," *Anal. Biochem.*, 273: 73-80 (1999).
Gleixner et al., "Detection of the anabolic beta-2-adenoreceptor agonist clenbuterol in human scalp hair by HPLC/EIA," *Clin. Chem.*, 1996, 42(11):1869-1871.
Gleixner, "Examination of calf hair for effective anabolic sex steroids Meaning for residue control," *Fleischwirtschaft*, 72(12): 1108-1110 (1997).
Gratacos-Cubarsi et al., "Assessment of enrofloxacin and ciprofloxacin accumulation in pig and calf hair by HPLC and fluorimetric detection," *Anal and Bioanalytical Chemistry*; 387(6); 1991-98 (2007)vol. 387.
Gratacos-Cubarsi, et al, "Traceability of sulfonamide antibiotic treatment by immunochemical analysis of farm animal hair samples," *Anal and Bioanalytical Chemistry*, 395(4): 1009-16 (2009).
Gratacos-Cubarsi, et al., "Detection of sulphamethazine residues in cattle and pig hair by HPLC-DAD," *J. Chrom B*, 832: 121-126 (Feb. 17, 2006).
Hernandez-Carrasquilla, "External contamination of bovine hair with $\beta_2$-agonist compounds: evaluation of decontamination strategies," *Journal of Chromatography B*, 767: 235-243 (2002).
Hongwu et al., "Parallel Detection and Quantification Using Nine Immunoassays in a Protein Microarray for Drug from Serum Samples," *Biomed. Microdev.*, 2005, 7(2):143-146.
Hongwu et al., "Preparation of Steroid antibodies and parallel detection of multianabolic steroid abuse with conjugated hapten microarray," *Analyt. Chem.*, 2004, 76(20):6166-6171.

(56) References Cited

OTHER PUBLICATIONS

Hooijerink et al., "Liquid chromatography-electrospray ionization-mass spectrometry based method for the determination of estradiol benzoate in hair of cattle," *Analytica Chimica Acta*, 529:167-172 (2005).

Jouvel et al., "Detection of diazepam in horse hair samples by mass spectrometric methods," Analyst, 125: 1765-1769 (2000).

Kintz et al., "Detection of Drugs in Human Hair using Abbot Adx, with confirmation by Gas Chromatography/Mass Spectrometery(GC/MS)," *Journal of Forensic Sciences*, 1992, 37(1): 328-331.

Mogos et al., "Evaluation of the metabolic balance in type 2 diabetes by assay of the hair glucose," *Rom. J. Intern. Med.*, 2003, 41:61-65.

Nielen et al., "Multi residue screening of intact testosterone esters and boldenone undecylenate in bovine hair using liquid chromatography electrospray tandem mass spectrometry," *J. Chromatography B*, 2006, 830:126-134.

Offidani et al., "Improved enzymatic hydrolysis of hair," *Forensic Science International*, 63: 171-174 (1993).

Paisey et al., "Glycosylation of hair: possible measure of chronic hyperglycaemia," *Br. Med. J. (Clin. Res. Ed.)*, 1984, 288:669-671.

Rambaud et al., "Study of 17β-estradiol-3-benzoate, 17α—methyltestosterone and medroxyprogesterone acetate fixation in bovine hair," *Analytica Chimica Acta*, 532: 165-176 (2005).

Stupar et al., "Longitudinal hair chromium profiles of elderly subjects with normal glucose tolerance and type 2 diabetes mellitus," *Metabolism*, 2007, 56(1): 94-104.

Suzuki et al., "Nails as useful materials for detection of methamphetamine or amphetamine abuse," *Forensic Sci. International*, 1984, 24:9-16.

Thieme et al, "Analytical strategy for detecting doping agents in hair," *Forensic Science International*, 107: 335-345 (2000).

Wurst et al., "Concentration of fatty acid ethyl esters in hair of alcoholics: comparison to other biological state markers and self reported-ethanol intake," *Alcohol and Alcoholism*, 2004, 39:33-38.

Extended European Search Report issued in European Application No. 13162193.0, dated Jul. 9, 2013, 4 pages.

Office Action in Chinese Application No. 200980126100.6, dated Apr. 26, 2013, 15 pages (with English translation).

Office Action in Japanese Application No. 2011-507600, dated Nov. 19, 2012, 15 pages (with English translation).

U.S. Appl. No. 13/931,169, filed Jun. 28, 2013, Hill et al.

U.S. Appl. No. 12/111,914, filed Oct. 29, 2009, Hill et al.

Baumgartner and Hill, "Hair Analysis for Drugs of Abuse: Decontaminations Issue," Recent Developments in Therapeutic Drug Monitoring and Clinical Toxicology, 1992, 577-597.

Baumgartner and Hill, "Hair Analysis for Organic Analytes: Methodology, Reliability Issues, and Field Studies," Drug Testing in Hair, 1996, 223-265.

Baumgartner and Hill, "Sample Preparation Techniques," *Forensic Science Int.* 63 (1993) 121-135.

Baumgartner et al., "Sample preparation techniques," in *Forensic Science International*, 63, Dec. 1, 1993, 121-131.

International Search Report and Written Opinion for International Application No. PCT/US2013/048661, dated Sep. 30, 2013, 11 pages.

U.S. Appl. No. 12/111,914, filed Dec. 27, 2011, Hill et al, now U.S. Pat. No. 8,084,215.

U.S. Appl. No. 13/336,119, filed Dec. 11, 2012, Hill et al, now U.S. Pat. No. 8,329,417.

U.S. Appl. No. 12/990,447, filed May 7, 2013, Hill et al, now U.S. Pat. No. 8,435,747.

U.S. Appl. No. 61/665,790, filed Jun. 28, 2012, Hill et al.

"Dithiothreitol (DTT)," *US Biological*, posted on or before Jan. 31, 2013, retrieved Dec. 15, 2014, http://web.archive.org/web/20130131042135/http://www.usbio.net/item/D8070, pages.

"DL-Dithiothreitol," *Sigma-Aldrich*, Apr. 2008, retrieved on Dec. 15, 2014, http://www.sigmaaldrich.com/content/dam/sigma-aldrich/docs/Sigma-Aldrich/Product_Information_Sheet/d0632pis.pdf1 page.

Butler et al., "The Immunochemistry of Sandwich ELISAs—VI. Greater than 90% of Monoclonal and 75% of Polyclonal Anti-Fluorescyl Capture Antibodies (Cabs) Are Denatured by Passive Adsorption," Molecular Immunology, 1993, 30(13): 1165-1175.

Fasano et al., "The Extraordinary Ligand Binding Properties of Human Serum Albumin," IUBMB Life, 57(12):787-796.

Gratacos-Cubarski et al., "Hair analysis for veterinary drug monitoring in livestock production," J. Chromatography B, 2006, 834:14-25.

Harriman et al., "Multiplexed Elispot Assay," J. Immunological Methods, 2009, 341:127-134.

Harriman et al., "Antibody Discovery via Multiplexed Single Cell Characterization," J. Immunol Methods, Feb. 2009, 241(1-2): 135-145.

Leow et al., "Determination of the Serum Protein Binding of Oxycodone and Morphine Using Ultrafiltration," Therapeutic Drug Monitoring, 1993, 15:440-447.

Panoyan et al., "Immunodetection of Clenbuterol in the Hair of Calves," J. Agric. Food Chem., 43: 2716-2718 (1995).

Parker et al., "Factors Affecting Serum Proteing Binding of Cocaine in Humans," J. Pharmacology and Experimental Therapeutics, 1995, 275(2):605-610.

Staub, "Analytical procedures for determination of opiates in hair: a review," For. Sci. Int., 70: 111-123 (1995).

Varshney et al., "Ligand Binding Strategies of Human Serum Albumin: How Can the Cargo by Utilized?" Chirality, 2009, 11 pages.

Canadian Office Action in Canadian Application No. 2723161, dated May 29, 2015, 6 pages.

Clerico, et al., "Immunoassay methods for the measurement of natriuretic cardiac hormones (ANP, BNP, and related peptides) in humans" J. Clin. Ligand Assay, 1999, 22:194-204.

Lyashchenko et al., "A multi-antigen print immunoassay for the development of serological diagnosis of infectious diseases," J. Immunological Methods, 2000, 242:91-100.

Price and Newman, Principles and Practice of Immunoassay, Second Edition, 1997, 4-7, 186-191.

Wild, "Comparison of Experimental and Theoretical Immunoassay Performance," The Immunoassay Handbook, 1994, 42-43.

Office Action in Indian Application No. 7597/CHENP/2010, dated Feb. 17, 2017, 10 pages.

Office Action in Chinese Application No. 201610077781.3, dated Jan. 25, 2017, 19 pages (with English translation).

\* cited by examiner

SOLID PHASE MULTI-ANALYTE ASSAY

CROSS-REFERENCE TO RELATED APPLICATIONS

This application is a National Stage application under 35 U.S.C. § 371 and claims the benefit under 35 U.S.C. § 119(a) of International Application No. PCT/US2009/042061, having an International Filing Date of Apr. 29, 2009, which claims the benefit of priority of the U.S. Provisional Application Ser. No. 61/048,892, having a filing date of Apr. 29, 2008, all of which are incorporated herein in their entirety.

TECHNICAL FIELD

This disclosure relates to methods and compositions for determining the presence and/or amount of one or more analytes (e.g., drugs of abuse, toxic chemicals, prescription medicines) in a sample (e.g., a bodily sample or a non-bodily sample), and more particularly to methods and compositions for doing the same using competitive immunoassays. In some embodiments, the methods and compositions can be used to determine the presence and/or amount of two or more analytes in a sample simultaneously, in tandem, or serially. Solid phase analyte compositions comprising two or more different analytes bound to a solid phase are described, as well as methods for using the same in competitive immunoassays, to determine the presence and amount of one or more analytes of interest.

BACKGROUND

Immunoassays such as radioimmunoassays (RIA) and enzyme immunoassays (EIA) are useful methods for determining the presence, identity, and amount of one or more analytes of interest in a sample. Many immunoassays immobilize an antibody specific for an analyte of interest on a solid phase, e.g., a microplate or bead; binding between the bound antibody and analyte present in a sample is detected, such as through the use of a sandwich assay. Other immunoassays immobilize the analyte; these immunoassays can be referred to as solid phase antigen or solid phase analyte immunoassays. In solid phase analyte immunoassays, the solid phase analyte competes with analyte present in a sample for binding to an antibody specific for the analyte. Typically in such solid phase analyte assays, the antibody is detectable in some manner, e.g., it is labeled, such as radioactively, fluorescently, luminescently, or enzymatically (e.g., an enzymatic reaction occurs in the presence of an appropriate substrate, resulting in a color change) labeled, or its presence is detected via a secondary antibody that itself is labeled.

In order to determine if a particular sample contained more than one analyte of interest, previous methods typically employed separate solid phase components (e.g., separate microplates or sets of microbeads), with each solid phase component containing a bound antibody specific for one particular analyte, or with each solid phase component containing a single type of bound analyte. Such a need for separate solid phase components for each analyte renders multi-analyte assays expensive, technically complex, and time-consuming. There exists a need for an efficient and relatively inexpensive analyte detection method that can rapidly determine the presence and/or amount of one or more analytes, including analytes such as drugs of abuse, in a sample.

SUMMARY

Immunoassays are powerful tools for detecting the presence and/or amount of analytes in, or suspected to be in, a sample. The ability to detect multiple analytes in a sample, however, typically requires the use of multiple separate assays, e.g., one per analyte of interest, thus increasing cost, time, and technical complexity of the procedure, and leading to potential operator errors during one of the multiple steps. The inventors have surprisingly found that the use of solid phase analyte compositions comprising at least two bound analytes to the solid phase facilitate the performance of multi-analyte assays exhibiting high sensitivities and efficiencies. The multi-analyte assays described herein are flexible, and can be performed simultaneously, serially, or in tandem, resulting in reduced cost, time, and complexity of the procedure.

Accordingly, provided herein is a method for determining the presence of an analyte of interest in a sample comprising:

(a) contacting a solid phase analyte composition, wherein the solid phase analyte composition comprises at least two different analytes associated with a solid phase support, wherein one of the at least two different analytes is the analyte of interest, with:

i) an antibody, wherein the antibody is specific for the analyte of interest; and ii) a sample; and (b) determining if the analyte of interest is present in the sample.

In some embodiments, the solid phase analyte composition is first contacted with the sample, and then with the antibody. In some embodiments, the antibody is detectably labeled, e.g., detectably labeled with a fluorescent, luminescent (including chemiluminescent or bioluminescent), radioactive, or enzymatic label. In some embodiments, the antibody is not labeled.

In some embodiments, the method comprises removing antibody that is not bound to the solid phase analyte composition.

In some embodiments, the method comprises determining the amount of analyte present, if the analyte is present.

In some embodiments, the analyte is determined to be present in the sample by comparing a signal generated by the antibody bound to the solid phase analyte composition in the sample with a signal generated by the antibody bound to the solid phase analyte composition in a control sample that does not comprise the analyte of interest.

In some embodiments, the signal generated by the antibody bound to the solid phase analyte composition is derived from a detectable label on the antibody.

In some embodiments, the signal generated by the antibody bound to the solid phase analyte composition is derived from the binding of a secondary antibody to the antibody, wherein the secondary antibody is detectably labeled.

In some embodiments, the detectable label is a fluorescent, luminescent (including chemiluminescent or bioluminescent), radioactive, or enzymatic label.

In some embodiments, the method further comprises contacting the solid phase analyte composition with a second antibody, where the second antibody is specific for the at least second different analyte associated with the solid phase, and determining if the second analyte is present in the sample.

In some embodiments of the method, the at least two different analytes are associated with the solid phase non-covalently, either directly or indirectly.

In some embodiments, the at least two different analytes are associated with the solid phase covalently, either directly or indirectly.

In some embodiments, the at least two different analytes are associated with the solid phase via adsorption, either directly or indirectly.

In some embodiments, the at least two different analytes are covalently linked to a binding agent which is associated with the solid phase noncovalently or via adsorption.

In some embodiments, the binding agent is selected from HSA and BSA.

In some embodiments, the at least two different analytes are drugs of abuse or metabolites thereof. A drug of abuse or metabolites thereof can be selected from cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA).

A sample can be a bodily sample or a sample derived from a bodily sample.

A bodily sample can be from a human, and is selected from a tissue sample of the brain, heart, lung, kidney, liver, muscle, bone, stomach, intestines, and skin; a biological fluid selected from urine, blood, plasma, serum, saliva, semen, sputum, cerebral spinal fluid, mucus, sweat, vitreous liquid, and milk; and a keratinized structure.

A solid support can be a microwell of a microplate.

Also provided is a method for determining the presence of a plurality of different analytes of interest, represented by the number "N", in a sample, the method comprising:

(a) contacting a solid phase analyte composition, wherein the solid phase analyte composition comprises at least "N" different analytes associated with a solid phase support, wherein the at least "N" different analytes associated include the plurality of analytes of interest, with:
  i) a plurality of antibodies, wherein the plurality of antibodies comprises an antibody specific for each different analyte of interest; and
  ii) a sample; and
(b) determining whether each different analyte of interest in the plurality is present in the sample.

In some embodiments, the antibodies specific for each different analyte of interest are separately detectable. In some embodiments, the antibodies are detectably labeled with a fluorescent, luminescent (including chemiluminescent or bioluminescent), radioactive, or enzymatic label.

In some embodiments, the method includes determining the amount of each different analyte of interest, if present.

In some embodiments, each different analyte of interest is determined to be present in the sample by comparing a signal generated by the antibody specific for a particular analyte of interest bound to the solid phase analyte composition in the sample with a signal generated by the same antibody bound to the solid phase analyte composition in a control sample that does not comprise the particular analyte of interest.

In some embodiments, the plurality of antibodies is contacted with the solid phase analyte composition simultaneously.

In some embodiments, at least one of the plurality of antibodies is contacted with the solid phase analyte composition at a time different than at least another of the plurality of antibodies.

Also provided is a composition comprising at least two different analytes associated with a solid phase. The at least two different analytes can be covalently bound to the solid phase, either directly or indirectly. The at least two different analytes can be noncovalently bound to the solid phase, either directly or indirectly.

In some embodiments, a composition comprises from 2 to 10 different analytes associated with a solid phase. In some embodiments, the at least two different analytes are drug of abuse analytes or metabolites thereof. In some embodiments, the at least two different analytes are selected from cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA).

Further provided is a kit comprising a composition as described herein, and at least one antibody specific for at least one of the two different analytes associated with the solid phase. In some embodiments, the kit can include at least one antibody specific for an analyte selected from the group consisting of: cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA).

Also provided is a method for determining the presence of an analyte of interest or one or more metabolites thereof in a sample comprising:

(a) contacting a solid phase analyte composition, wherein the solid phase analyte composition comprises at least two different analytes associated with a solid phase support, wherein one of the at least two different analytes is the analyte of interest, with:
  i) an antibody, wherein the antibody is specific for the analyte of interest and is further capable of binding to one or more metabolites of the analyte of interest; and
  ii) a sample; and
(b) determining if the analyte of interest or one or more metabolites thereof is present in the sample.

Further provided is a method for determining the presence at least one member of a drug class of interest in a sample comprising:

(a) contacting a solid phase analyte composition, wherein the solid phase analyte composition comprises at least two different analytes associated with a solid phase support, wherein one of the at least two different analytes is a member of the drug class of interest, with:
  i) an antibody, wherein the antibody is specific for the member of the drug class of interest and is further capable of binding to one or more other members of the drug class of interest or to one or more metabolites of a member of the drug class of interest; and
  ii) a sample; and
(b) determining if at least one member of the drug class of interest is present in the sample.

In any of the methods, the at least two different analytes can be selected from drugs of abuse, toxic chemicals, environmental chemicals, petroleum products, natural products, organic compounds, nutrients, prescription and over-the-counter medications, or metabolites, derivatives, or breakdown products of any of the foregoing.

In some embodiments of the methods, the at least two different analytes can be selected from opioids, amphetamines, NSAIDS, steroids, cannabinoids, benzodiazepines, barbiturates, tricyclics, and ephedrines, or metabolites, derivatives, or breakdown products of any of the foregoing.

In some embodiments of the compositions, the at least two different analytes can be selected from drugs of abuse, toxic chemicals, environmental chemicals, petroleum products, natural products, organic compounds, nutrients, prescription and over-the-counter medications, or metabolites, derivatives, or breakdown products of any of the foregoing.

In some embodiments of the compositions, the at least two different analytes are selected from opioids, amphetamines, NSAIDS, steroids, cannabinoids, benzodiazepines, barbiturates, tricyclics, and ephedrines, or metabolites, derivatives, or breakdown products of any of the foregoing.

In some embodiments of the kits, the composition comprises at least two different analytes selected from drugs of abuse, toxic chemicals, environmental chemicals, petroleum products, natural products, organic compounds, nutrients, prescription and over-the-counter medications, or metabolites, derivatives, or breakdown products of any of the foregoing.

In some embodiments of the kits, the composition comprises at least two different analytes selected from opioids, amphetamines, NSAIDS, steroids, cannabinoids, benzodiazepines, barbiturates, tricyclics, and ephedrines, or metabolites, derivatives, or breakdown products of any of the foregoing.

Unless otherwise defined, all technical and scientific terms used herein have the same meaning as commonly understood by one of ordinary skill in the art to which this disclosure pertains. Although methods and materials similar or equivalent to those described herein can be used in the practice or testing of the presently described methods, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DETAILED DESCRIPTION

Figure 1:
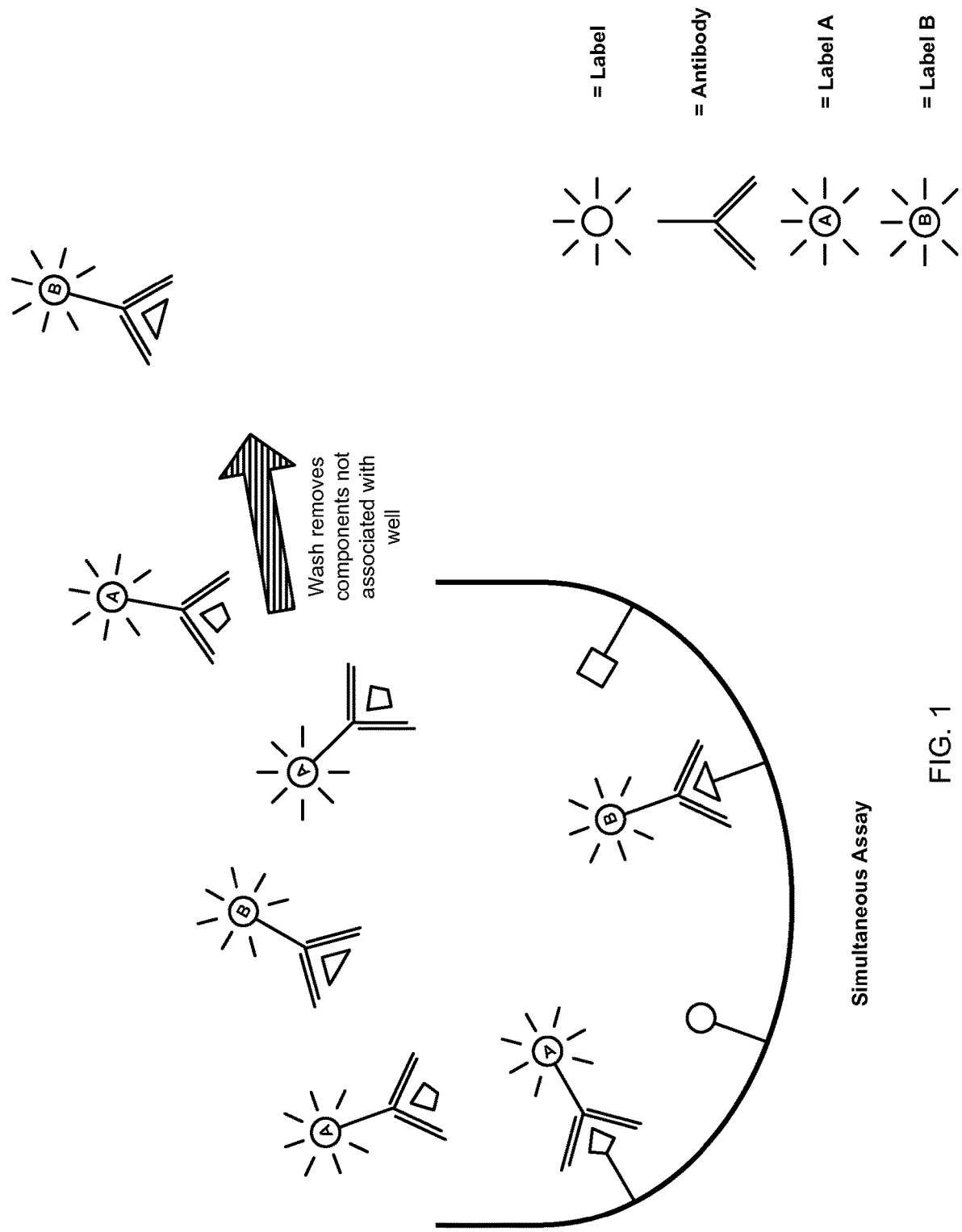
FIG. 1 is a schematic of a solid phase composition provided herein (e.g., a microwell of a microplate) having at least two different analytes bound thereto, represented in the figure by triangles, squares, circles, diamonds. The schematic demonstrates the ability of the present solid phase compositions and methods to determine the presence and/or amount of two or more analytes simultaneously. For example, diamond and triangle analytes present in a sample compete with diamond and triangle analytes bound to the solid phase for binding to labeled antibodies specific for the diamond and triangle analytes, respectively, resulting in a loss of signal, e.g., after a wash step. Antibodies specific for diamond and triangle analytes can be differentially labeled (i.e., as labels A and B here, respectively), allowing for separate detection of the diamond and triangle analytes.

Provided herein are materials and methods for the rapid, sensitive, and cost-effective detection of one or more different analytes in a sample using a solid phase analyte composition having at least two different analytes associated with a solid phase. The materials and methods take advantage of the surprising efficiencies and sensitivities generated by binding two or more different analytes to a single solid phase component. For example, a microplate wherein each microwell has the same two or more different analytes bound thereto can be used to determine the presence and/or amount of the two or more different analytes in a sample in a single microwell by using a differentially labeled antibody for each of the two or more analytes of interest in a competitive immunoassay; by probing for the differential signal of each specific antibody, the presence and/or amount of the analyte for which it is specific can be determined.

In other embodiments, the solid phase analyte compositions can be used to determine the presence and/or amount of two or more different analytes by separately detecting the two or more different analytes using separate (but having the same set of two or more analytes bound) solid phase analyte compositions and the appropriate labeled antibody specific for the analyte of interest (e.g., a tandem or side-by-side assay). In yet other embodiments, the same solid phase composition can be used to determine the presence and/or amount of two or more different analytes by first using the solid phase analyte composition to determine the presence and/or amount of at least a first analyte using an antibody specific for the at least first analyte, and then using the same solid phase composition to determine the presence and/or amount of the at least second analyte using an antibody specific for the at least second analyte, e.g., either immediately or after removal of any interfering substances from the first assay. Such assay formats can be referred to as serial assays.

Compositions

Provided herein are compositions useful for detecting (e.g., determining the presence and/or amount of) one or more different analytes of interest in a sample. The compositions include a solid phase support associated with at least two analytes, e.g., 2, 3, 4, 5, 6, 7, 8, 9, 10, 11, 12, 13, 14, 15, 16, 17, 18, 19, or 20 analytes, or more. In some embodiments, from 2 to 5 analytes are associated with the solid phase support. In other embodiments, 5 to 10 analytes are associated with the solid phase support. Such compositions are referred to as solid phase analyte compositions herein.

As will be evident to those having ordinary skill in the art, although the compositions make it possible to determine the presence and/or amount of the total number of different analytes ("N") associated with the solid phase support, one need not determine (or evaluate) the presence and/or amount of all analytes that are possible to be determined with a given solid phase analyte composition. For example, in some embodiments, it may be useful to determine the presence and/or amount of only one analyte of interest. In other embodiments, it may be useful to first determine if one or more analytes of interest is/are present, followed by determining if a second or more analytes is/are present. The solid phase compositions described herein facilitate the simultaneous, tandem, or serial detection of up to the number of analytes "N" associated with the solid phase.

As used herein, the phrases "determine the presence" and "determining the presence" mean determining whether or not an analyte is present. Thus, if an analyte is determined to be absent, such an activity would still be encompassed by the phrases.

An analyte can be any chemical, including drugs of abuse, toxic chemicals, environmental chemicals (e.g., pesticides, herbicides, insecticides), petroleum products, natural products, organic compounds, nutrients, prescription or over-the-counter medications (e.g., pain medications, steroids, narcotics, NSAIDS), or metabolites, derivatives, or breakdown products of any of the foregoing.

In some embodiments, analytes for association with a solid phase support are drugs, such as drugs of abuse, prescription medications, or pain medications. Particular drug classes of interest include opioids, steroids, amphetamines, cannabinoids, benzodiazepines, NSAIDS, barbiturates, tricyclics, and ephedrines.

In some embodiments, an analyte of interest can be selected from: cocaine (and metabolites benzoylecgonine, cocaethylene, and norcocaine), opioids and metabolites thereof (morphine, heroin, 6-monoacetylmorphine, diacetylmorphine, codeine, oxycodone, hydrocodone, hydromorphone, oxymorphone, and methadone), phencyclidine (PCP), amphetamines, methamphetamines, MDMA (ecstasy, methylenedioxy-methamphetamine), MDA (methylenedioxyamphetamine), cannabinoids (and THC and carboxy-THC metabolites), propoxyphene, meperidine, benzodiazepines (alprazolam, chlordiazepoxide, diazepam, lorazepam, flunitrazepam, triazolom, and estazolam), barbiturates (mephobarbital, pentobarbital), carisoprodol, tramadol, fentanyl, buprenorphine, naltrexone, tricyclics, nicotine (and its metabolite cotinine), eve (methylenedioxy-ethylamphetamine), lysergic acid (LSD), digoxin, methylphenidate, acetaminophen, salicylates, fluoxetine, sertraline, dextromethorphan, ephedrine, phenethylamines, pseudoephedrine, and synephrine.

In some embodiments, analytes for association with a solid phase support are drugs of abuse or metabolites thereof, and can be selected from the following: cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA).

In particular embodiments, a composition can include at least two of: cocaine, one or more opioids, PCP, amphetamines, and cannabinoids associated with the solid support. In particular embodiments two or more of pain management medications selected from morphine, codeine, oxycodone, oxymorphone, hydrocodone, or hydromorphone can be associated with the solid support. In some embodiments, two or more of cocaine and an opioid can be associated with the solid support.

Any type of sample can be tested for the presence and/or amount of one or more analytes of interest. In certain cases, a sample contains or is suspected to contain one or more analytes of interest, such as one or more drugs of abuse or toxic chemicals. A sample can be a bodily sample or a non-bodily sample. A bodily sample can be a specimen obtained from an individual (e.g., a human, mouse, rat, pig, horse, monkey, rabbit, cow, sheep, or goat). A bodily sample can be a tissue sample, such as a tissue sample of the brain, heart, lungs, kidneys, liver, muscle, bone, stomach, intestines, or skin. A bodily sample can be obtained by biopsy or from tissue culture. A bodily sample can include a biological fluid such as urine, blood, plasma, serum, saliva, semen, sputum, cerebral spinal fluid, mucus, sweat, milk, vitreous fluid and the like. A bodily sample can be a keratinized structure, such as hair, a fingernail, or a toenail. A non-bodily sample can be, for example, a soil or water sample, a plant sample, an inorganic material sample, or a sample from a research or manufacturing process.

A sample can be used as is, or can be treated to result in a final sample for detection of the one or more analytes. For example, a sample can be liquefied, concentrated, dried, diluted, lyophilized, extracted, fractionated, subjected to chromatography, purified, acidified, reduced, degraded, subjected to enzymatic treatment, or otherwise treated in ways known to those having ordinary skill in the art in order to release an analyte of interest. If desired, a sample can be a combination (pool) of samples, e.g., from an individual or from a manufacturing process.

A sample can be in a variety of physical states, e.g., liquid, solid, emulsion, or gel. Samples can be treated with customary care to preserve analyte integrity. Treatment can include the use of appropriate buffers and/or inhibitors, such as inhibitors of certain biological enzymes. One having ordinary skill in the art will be able to determine the appropriate conditions given the analytes of interest and the nature of the sample.

As used herein, the terms "solid phase" and "solid phase support" are used interchangeably, and refer to any solid or semi-solid material with which two or more analytes can be associated, e.g., a material to which they can be attached covalently or noncovalently, either directly or indirectly, or a material in which they can be incorporated (e.g., physical entrapment, adsorption, etc.), or a material which can be functionalized to include (e.g., to associate with) the two or more analytes. In addition to the analytes, a solid phase support can contain a variety of materials including, e.g., a natural or synthetic polymer, resin, metal, or silicate.

Suitable solid phase supports are known in the art and illustratively include agaroses (commercially available as Sepharose); celluloses (e.g., a carboxymethyl cellulose); dextrans, (such as Sephadex); polyacrylamides; polystyrenes; polyethylene glycols; resins; silicates; divinylbenzenes; methacrylates; polymethacrylates; glass; ceramics; papers; metals; metalloids; polyacryloylmorpholidse; polyamides; poly(tetrafluoroethylenes); polyethylenes; polypropylenes; poly(4-methylbutenes); poly(ethylene terephthalates); rayons; nylons; poly(vinyl butyrates); polyvinylidene difluorides (PVDF); silicones; polyformaldehydes; cellulose acetates; nitrocellulosse, or combinations of two or more of any of the foregoing. All that is required is that the material or combination of materials in the solid phase support not substantially interfere, e.g., in some cases only minimally interfere, with the binding between the two or more analytes and the antibodies specific for each analyte.

A solid phase support can have a variety of physical formats, which can include for example, a membrane; a chip; a slide (e.g., a glass slide or coverslip); a column; a hollow, solid, semi-solid, pore or cavity containing particle such as a bead; a gel; a fiber including a fiber optic material; a matrix; and a sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, multiwell or microwell plate, and the like. A particle to which an analyte is associated with can have a variety of sizes, including particles that remain suspended in a solution of desired viscosity, as well as particles that readily precipitate in a solution of desired viscosity. Particles can be selected for ease of separation from sample constituents, for example, by including purification tags for separation with a suitable tag-binding material, paramagnetic properties for magnetic separation, and the like.

Generally, a particle described herein has a spherical shape. However, a particle can be, e.g., oblong or tube-like. In some embodiments, e.g., a crystalline form particle, the particle can have polyhedral shape (irregular or regular), such as a cube shape. In some embodiments, a particle can be amorphous.

In some embodiments, a particle mixture can be substantially spherical, substantially oblong, substantially tube-like, substantially polyhedral, or substantially amorphous. By "substantially" is meant that the particle mixture is more than 30 (e.g., 35, 40, 45, 50, 55, 60, 65, 70, 75, 80, 85, 90, 95, 96, 97, 98, or 99 or more) % of a given shape.

In some embodiments, the diameter (or longest straight dimension) of the particle can be between about 1 nm to about 1000 nm or larger. For example, a particle can be at least about 1 nm to about 1000 nm (e.g., at least about two, three, four, five, six, seven, eight, nine, 10, 15, 20, 25, 30, 35, 40, 45, 50, 75, 100, 150, 200, 250, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nm). In some embodiments, a particle can be not more than 1000 nm (e.g., not more than 975, 950, 925, 900, 875, 850, 825, 800, 775, 750, 725, 700, 675, 650, 625, 600, 575, 550, 525, 500, 475, 450, 425, 400, 375, 350, 325, 300, 275, 250, 225, 200, 175, 150, 125, 100, 75, 50, 45, 40, 35, 30, 25, 20, 15, 10, or five nm) in diameter (or at its longest straight dimension).

Suitable methods for producing solid-phase supports, as well as additional examples of solid-phase supports (e.g., particles) for use in the compositions and methods described herein, can be found in, e.g., PCT Publication Nos. WO 01/84157, WO 99/30160, WO 99/42838, and WO 06/078618, the disclosures of each of which are incorporated by reference in their entirety.

An analyte can be associated with a solid phase support in a number of ways known to those having ordinary skill in the art. For example, an analyte can be covalently or non-covalently bound to a solid-phase support, either directly or indirectly, such as through a linker, binding agent, or member of a binding pair. For example, an analyte can be directly covalently bound to a solid phase support, e.g., through a chemical bond between a functional group on the analyte and a functional group on the solid phase support. Alternatively, an analyte can be indirectly covalently bound to a solid-phase support, e.g., an analyte can be covalently bound to a linker or binding agent, which itself is covalently bound to the solid phase support. In some embodiments, an analyte is directly non-covalently bound to a solid phase support, e.g., noncovalent association or adsorption of the analyte on the solid phase support. In other embodiments, an analyte is indirectly noncovalently bound to a solid phase support, e.g., is covalently bound to a linker, binding agent, or member of a binding pair, which noncovalently associates with the solid phase support. In all cases, association of an analyte of interest with a solid phase should not substantially affect, e.g., should only minimally affect, the specificity of an antibody for the associated analyte as compared to the specificity for the analyte when it is not associated with a solid phase.

A variety of chemical reactions useful for covalently attaching an analyte to a support are well known to those skilled in the art (see, for example, Hartmann et al. (2002) J. Mater. Res. 17(2):473-478). Illustrative examples of functional groups useful for covalent attachment to a support include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity.

An analyte can be noncovalently bound to a solid support, such as through adsorption to or coating on the solid phase support, or through covalent or noncovalent association with a linker, binding agent, or member of a binding pair, which itself is noncovalently bound or associated with the solid support. Illustrative examples of linkers, binding agents, or members of binding pairs useful for association of analytes to a support include proteins, organic polymers (PEG and derivatives thereof), and small molecules. Particular preferred examples include HSA, BSA, streptavidin, avidin, biotin, PEG, and antibodies or antibody fragments.

For example, in one preferred embodiment, an analyte can be covalently conjugated to a binding agent such as HSA or BSA, and then the resulting covalent conjugate can be used to noncovalently coat a solid support. In another embodiment, an analyte can be covalently conjugated to one member of a biotin and avidin binding pair; the covalent conjugate can then non-covalently bind to the other member of the binding pair, which can be noncovalently associated with (e.g., coated on) a solid support. In other embodiments, a covalent conjugate of an analyte with one member of a binding pair can bind noncovalently to the other member of the binding pair, which has been covalently linked to the solid support.

Linkers or binding agents can also be useful to covalently link an analyte to a solid support. For example, a covalent conjugate of an analyte with a binding agent such as HSA or BSA can be covalently linked to the solid support.

In some embodiments, the surface of the solid-phase support can be modified to facilitate the stable attachment of linkers or binding agents. Generally a skilled artisan can use routine methods to modify a solid-phase support in accordance with the desired application. The following are non-limiting examples of solid-phase support modifications.

The surface of the solid-phase support can, e.g., have a coating that facilitates the attachment to the analyte. In general, the coating will be one that is complementary to a linker moiety on the analyte. The surface of a solid-phase support can be amidated, e.g., by silylating the surface, e.g., with trialkoxyaminosilane. Silane-treated supports can also be derivatized with homobifunctional and heterobifunctional linkers. The support can be derivatized, e.g., so it has a hydroxy, an amino (e.g., alkylamine), carboxyl group, N-hydroxy-succinimidyl ester, photoactivatable group, sulfhydryl, ketone, or other functional group available for reaction. The supports can be derivatized with a mask in order to only derivatize limited areas (e.g., certain wells of a multiwell assay plate) or a chemical etch or UV light can be used to remove derivatization from selected regions.

The functional groups, instead of being coated on the surface, can be incorporated into the first solid-phase support either during or after the preparation of the first solid-phase support. The functional groups are usually chosen to dissolve in one or more components of the first solid-phase support but may be covalently attached to the first solid-phase support.

Additional methods for attaching an analyte to a solid-phase support are described in, e.g., PCT Publication Nos. WO 01/84157, WO 99/30160, and WO 06/078618, the disclosures of each of which are incorporated by reference in their entirety.

As described herein, two or more analytes are associated with the solid phase support. The type of association of each of the two or more analytes with the solid phase support can be the same or different relative to the association of the other analytes. For example, one analyte can be directly covalently bound, while another is indirectly covalently bound through a linker moiety. In another embodiment, one analyte can be covalently bound to a binding agent such as BSA, which is noncovalently bound to a solid phase support, while another analyte is directly covalently bound to the solid phase support. All that is required is that the separate associations do not interfere (e.g., do not interfere substantially) with the binding of an analyte with the antibody specific for the analyte.

The solid phase compositions comprising two or more different analytes associated with the solid phase can be surprisingly robust, e.g., can be stable for an extended period of time at room temperature. In some embodiments, the solid phase compositions described herein can be frozen, lyophilized, or immobilized and stored under appropriate conditions. Conditions should be such as to allow the analytes to retain activity.

Figure 2:
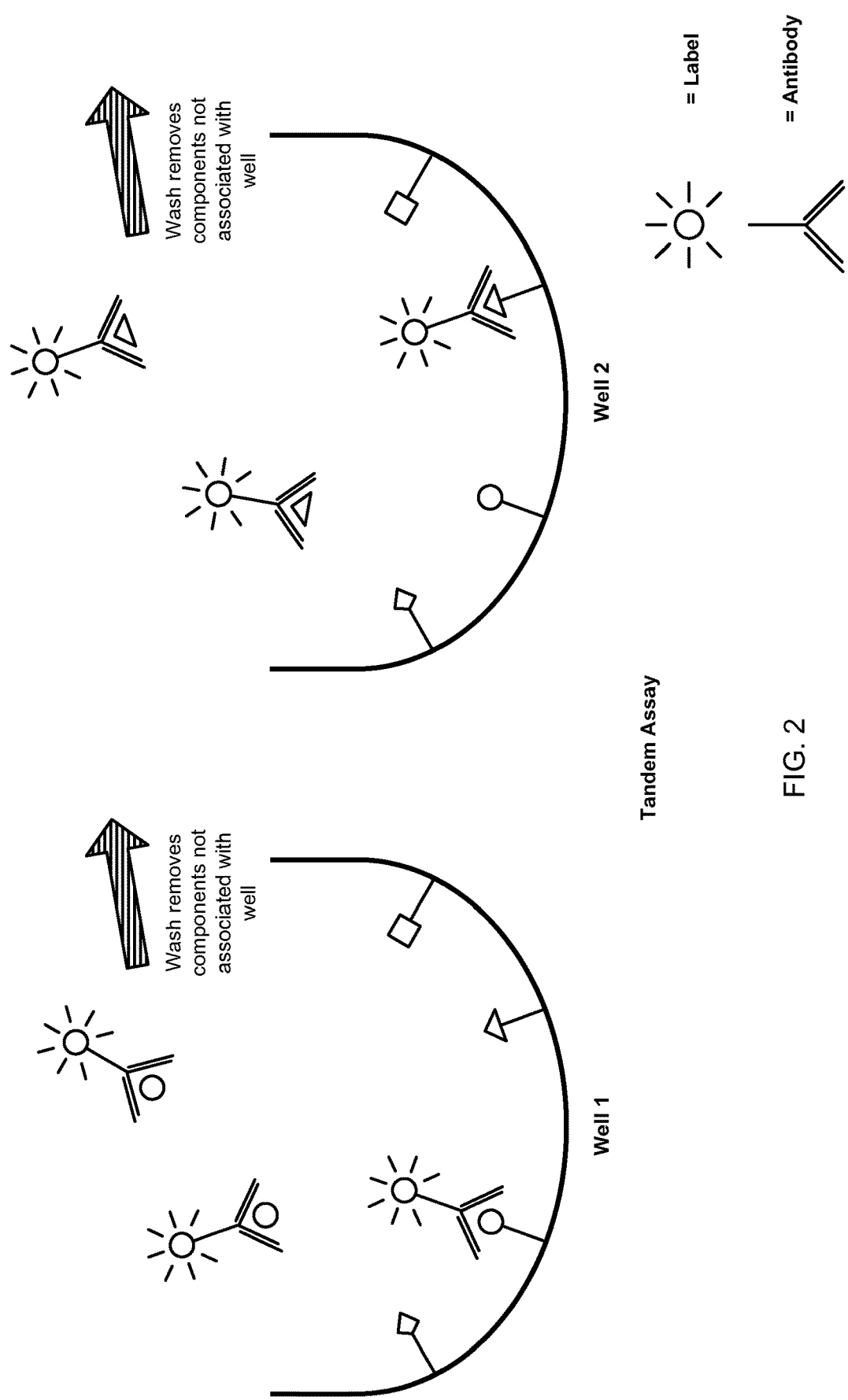
FIG. 2 is a schematic demonstrating a tandem assay using the solid phase compositions provided herein. In a tandem assay, the presence and/or amount of at least one analyte in a sample is detected (or tested for) using a solid phase composition provided herein (e.g., a microwell having at least two different analytes bound thereto, with at least one of the analytes bound being the one that is being tested for), while at least one different analyte is detected (or tested for) using a separate solid phase composition (e.g., an adjacent microwell having the same at least two different analytes bound thereto, with at least one of the analytes bound being the at least one different analyte tested for). In the figure, both well 1 and well 2 have the same four analytes bound thereto. In well 1, a competitive assay to detect the circle analyte in a sample is demonstrated, while in well 2 (e.g., an adjacent well), a competitive assay to detect the triangle analyte in a sample is demonstrated.
Figure 3:
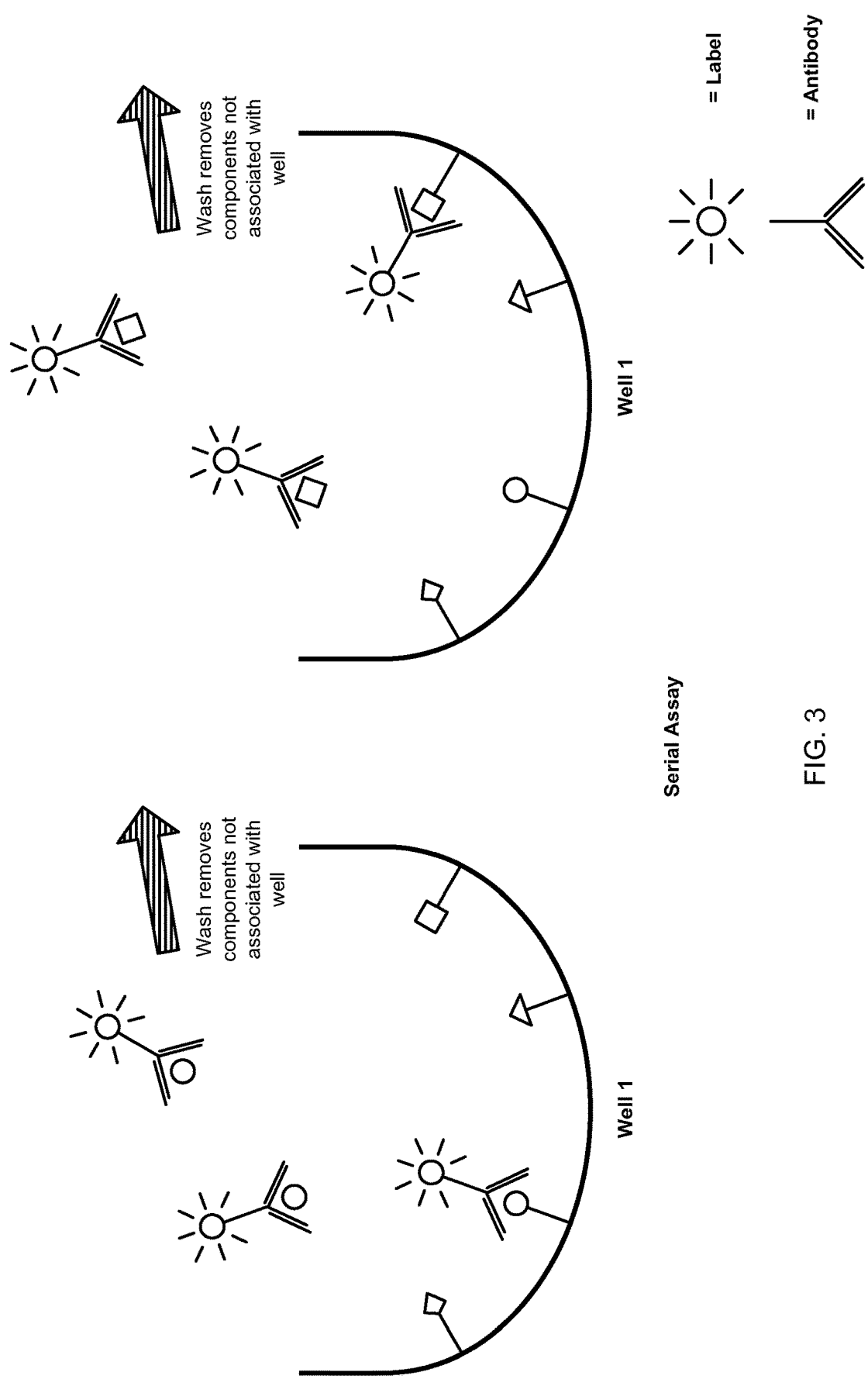
FIG. 3 is a schematic demonstrating a serial assay using the solid phase compositions provided herein. In a serial assay, at least one analyte in a sample is detected (or tested for) using a solid phase composition provided herein, followed by detection of (or testing for) at least one different analyte using the same solid phase composition. For example, in the figure, well 1 is first used to detect a circle analyte at t=1, followed by detection of a square analyte at t=2. Antibodies specific for the circle analyte can be removed prior to performance of the second assay at t=2; in some embodiments, the antibodies specific for the circle analyte can remain during the second assay, e.g., if they are differentially labeled from antibodies specific for the square analyte or otherwise do not interfere with detection of the square analyte.

Exemplary solid phase compositions are set forth in FIGS. 1-3 and are described below.

Applications

The technology described herein relates to determining the presence and/or amount of one or more analytes of interest. Generally, the methods involve competitive immunoassays, which are methods well known to those having ordinary skill in the art. In the competitive immunoassays employed herein, an analyte bound to a solid phase competes with an analyte present in a sample solution (e.g., a test sample) for binding to an antibody, such as a labeled antibody. The signal generated by the antibody after application of the sample to the solid phase composition can be compared to that generated after application of a control sample, or prior to application of the test sample, allowing determination of the presence of an analyte. Importantly, the present compositions and methods surprisingly allow the simultaneous or serial detection of two or more analytes, if desired, with high sensitivity and minimal interference from the other analytes.

In the methods, a solid-phase analyte support is prepared by associating a solid phase, such as a particle or multiwell of a multiwell plate, with at least two analytes. The solid phase analyte support is then contacted with one or more antibodies, wherein at least one antibody is specific for one of the two analytes associated with the solid composition, and also contacted with a sample (e.g., a test sample), which can contain or can be suspected to contain one or more analytes of interest. Typically, the antibody is detectably labeled (e.g., radioactively, fluorescently, luminescently, or enzymatically), or can be detected via the use of a secondary antibody that binds to the first antibody using methods (e.g., enzymatic amplification methods) known to those having ordinary skill in the art. In such methods, interaction of the antibody with the analyte for which it is specific results in the generation of a detectable signal, e.g., via the detectable label on the antibody or via a label on the secondary antibody. The signal is measured as a read-out of the presence or amount of the analyte.

An antibody for use in the methods can be any antibody that is specific for an analyte of interest. The term includes an antibody or analyte-binding fragment thereof. The term also encompasses a humanized antibody, a fully human antibody, a single chain antibody, a chimeric antibody, an $F_{ab}$ fragment, an $F_{(ab')2}$ fragment, an $F_{ab'}$ fragment, an $F_v$ fragment, and an $scF_v$ fragment. Antibodies to an analyte of interest can be obtained commercially from a number of sources or can be prepared and isolated using methods known to those having ordinary skill in the art, e.g., isolating the antibody from a host animal (e.g., a mammal such as a rat, rabbit, mouse, goat, cow, horse, dog, cat, sheep, donkey, chicken or a human) or cell (e.g., a hybridoma) that produces the antibody.

In some embodiments, the antibody is specific for the analyte of interest and is further capable of binding to one or more metabolites of the analyte of interest. For example, an antibody can be specific for cocaine, yet can demonstrate cross-reactive binding with one or more of cocaine's metabolites. In such cases, the cross-reactive binding should be sufficient to detect the one or more metabolites using the methods described herein.

Similarly, an antibody may be specific for a member of a drug class of interest and may be further capable of binding to one or more members of the drug class of interest and/or their metabolites. For example, an antibody may be specific for a particular opioid, yet can demonstrate cross-reactive binding to other opioids. In such cases, the cross-reactive binding should be sufficient to detect the one or more drugs or drug metabolites within the drug class using the methods described herein.

A method to determine the presence and/or amount of one or more analytes is carried out as follows. A solid phase analyte composition, as described above, such as a microplate comprising a microwell having at least two different analytes associated with each microwell, is contacted with i) at least one antibody, wherein the at least one antibody is specific for an analyte of interest; and ii) a sample, as described previously. Contacting can include any method of contacting, e.g., manually pipetting, washing, robotic or automated dispensing mechanisms, or other methods known to those having ordinary skill in the art. Routine care in the methods of contacting, e.g., sterile techniques or other methods to preserve sample integrity are understood by those having ordinary skill in the art.

The solid phase analyte composition may be first contacted with the antibody, and then with the sample, or vice versa. A known amount of antibody may be contacted with the solid phase composition, e.g., in quantitative methods.

Typically, the antibody is detectably labeled and the label enables the determination of the presence of the analyte. For example, the antibody can be detectably labeled with a fluorescent, luminescent (including chemiluminescent or bioluminescent), radioactive, or enzymatic label. In other cases, the antibody is not labeled, but is detected via the use of a secondary antibody that itself is labeled (e.g., enzymatically labeled) and that is specific for the first antibody. In cases where multiple analytes are detected simultaneously, the separate antibodies to each analyte of interest are preferably differentially labeled so that each can be detected separately from the others, e.g., through the use of fluorescent labels having non-overlapping absorption/emission spectra. Methods for detection, including automated methods, are well known to those having ordinary skill in the art.

Any of the methods can employ the use of a wash step, e.g., to remove antibody and analytes not bound to the solid phase analyte composition. Suitable wash conditions can be determined by those having ordinary skill in the art and should not substantially interfere, or only minimally interfere, with the binding of the antibody to the associated analyte on the solid phase.

The analyte can be determined to be present in the sample by taking advantage of the competitive nature of the assay. For example, the analyte can be determined to be present by comparing a signal generated by the antibody (e.g., from a fluorescent label on the antibody) bound to the solid phase analyte composition after contacting with the sample (e.g., the test sample) with a signal generated by the antibody bound to the solid phase analyte composition after contacting with a control sample that does not comprise the analyte of interest.

In any method, the solid phase analyte composition can be contacted with a second antibody, where the second antibody is specific for a second different analyte associated with the solid phase. The second antibody can be contacted at the same time as the first antibody (e.g., in a simultaneous assay for two analytes), or serially (e.g., in assays wherein it is desired to determine the presence of a first analyte prior to determination of a second analyte). As one having ordinary skill in the art will recognize, conceivably up to N antibodies, corresponding to the number of analytes associated with the solid phase, can be employed in the method, where the antibody population includes at least one antibody specific for each analyte associated. Moreover, while up to N analytes can be detected in a simultaneous assay, any smaller number can be detected in any assay, or any combination can be detected, e.g., in a simultaneous or serial assay. In addition, in certain embodiments, such as those employing microwell plates, one microwell may be used to test for one or more analytes of interest, while another microwell may be used to test for the same set of analytes of interest, a different set of analytes of interest, or an overlapping but not identical set of analytes of interest.

Kits

Also provided herein are kits, such as kits that include one or more solid phase analyte compositions described herein. The kits can include additional components, including buffers, reagents, instructions for use, and one or more antibodies for use in the methods. In some embodiments, at least one antibody specific for an analyte selected from the group consisting of cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA) is included in a kit. In some embodiments, the kits may include additional reagents for sample preparation, including reagent to extract or treat a sample for use in the methods.

EXAMPLES

Example 1: Reductive Extraction of Analytes from Hair and Detection of Multiple Analytes Using Solid Phase Compositions Having Multiple Analytes Bound Thereto Hair samples were analyzed for the presence of multiple analytes (e.g., drugs of abuse) using extraction methods as disclosed in U.S. application Ser. No. 12/111,914, entitled "Non-Proteolytic Method For The Determination Of Analytes In Keratinized Structures," (disclosing nonproteolytic reductive methods for extracting analytes from hair), filed simultaneously herewith on Apr. 29, 2008. Results obtained using such nonproteolytic reductive methods were also compared with results obtained using methods as disclosed in U.S. Pat. Nos. 6,022,693; 6,350,582; and 6,949,344 (disclosing combined proteolytic and reductive methods for extracting analytes from hair). Once extracted, the test samples were evaluated for the presence of multiple drug of abuse analytes using the methods and compositions disclosed herein, e.g., contacted with a solid phase having bound thereto two or more analytes and with one or more primary antibodies, each specific for a particular analyte; each primary antibody is then detected, e.g., through a label on the primary antibody or through detection of the primary antibody via a labeled secondary antibody.

I. Solutions
Solution to Digest a Hair Sample:
  1.5% solution of Dithiothreitol in water, pH 9.45-9.55
Solution to Neutralize a Digested Hair Sample:
1. 5% Zinc Chloride in water.
2. 1.0 M Bis Tris pH 7
3. Immediately prior to use, dilute the Zinc Chloride 1:10 in the Bis-Tris.
II. Treatment Procedure for Analyte Extraction for Enzyme Immunoassay (EIA)
  8 mg of hair samples was placed in test tubes with 0.8 mL of 1.5% Dithiothreitol solution, pH 9.5, and the samples incubated at 37° C. for 2 hours. Samples were neutralized with 70 µL of Zinc Chloride in Bis-Tris, mixed well and centrifuged.
III. Enzyme Immunoassay (EIA) Using Multi Analyte Coated Microplates and Using Dithiothreitol Extracts of Hair: Cocaine, Opioids, Amphetamines, PCP
  A. Preparation of Microplates: Coating with BSA Analyte Conjugates
  BSA (Bovine serum albumin) conjugates of the drugs of interest purchased from East Coast Biologicals were prepared in water. BSA conjugates (BSA-benzoylecgonine, BSA-morphine, BSA-PCP, BSA-methamphetamine) were dissolved in water such that from 1-10 ng of each of the analytes was present in 50 µL of drug conjugate solution.
  To coat the wells, fifty µL per well of the drug conjugate solution containing BSA-conjugates of benzoylecgonine, morphine, PCP, and methamphetamine were added to the wells on a 96-well microplate (high binding microplate from Corning Scientific). The plate was covered and placed on a rotator overnight at room temperature (RT) with rotation at about 100 cycles/min.
  After overnight rotation, the analyte mixture was removed and the wells washed once with PBS (phosphate buffered saline). To block the wells, 300 µL PBS containing 1% BSA were added to all wells, and the microplates rotated at RT for 4-6 hours (rotation speed about 100 cycles/min).

After blocking, the wells were washed 6 times with PBS containing 0.01% Tween-20. After washing, the plates were inverted and rapped against the counter to remove any liquid. The plates were then left inverted to dry on the bench for a few hours or overnight. When dry, they were placed in desiccated sealable vacuum bags; the air was withdrawn from the bag with a vacuum pump and the bag was sealed for storage.

B. Analysis

Aliquots of the digested and neutralized hair samples were combined in the microplate wells with an appropriate primary antibody directed against the analyte(s) of interest. After a 1-hour incubation at RT, the plates were washed with PBS on an automated plate washer. Following the wash, secondary antibody (directed against the primary antibody species) linked to HRP (horseradish peroxidase) was added to the wells and the plates incubated at RT for an hour. The plates were washed again, and substrate (TMB, 3,3',5,5', trimethylbenzidine) incubated in the wells for 30 minutes. Finally, 50 uL 4 NHCL was added and the absorbance read at 620 mu.

1. Cocaine in Hair: Solid-Phase Analyte Enzyme Immunoassay (EIA)

Example Result for Cocaine by Solid-Phase-Antigen EIA

| Sample | Percent* | MS Results**, ng/10 mg hair | | | |
|---|---|---|---|---|---|
| | | COC | BE | CE | NOR |
| Negative (Bo) | 100 | | | | |
| Cutoff (5 ng/10 mg hair) | 53.9 | | | | |
| Positive Sample 59498 | 12.5 | 31.6 | 13 | 6.3 | 1.1 |
| Positive Sample 59501 | 22.3 | 12.7 | 0.7 | 0 | 0 |
| Positive Sample 59571 | 27.8 | 9.4 | 1.3 | 0 | 0.3 |
| Negative Sample 59718 | 97.5 | | | | |
| Negative Sample 59708 | 91.3 | | | | |
| Negative Sample 58714 | 94.6 | | | | |
| Minus 50% control | 61.5 | | | | |
| Plus 50% control | 44 | | | | |

*Note:
Percent B/Bo for EIA -- The Negative (Bo) value of 100% is the reference tube containing no analyte in the sample and exhibits maximum binding of antibody to antigen. Unknown samples are expressed as percent of the Negative Bo, termed "Percent B/Bo." Concentrations of analyte in the samples vary inversely with Percent B/Bo values. A positive sample is one containing drug equal to or more than the cutoff calibrator and thus a Percent B/Bo equal to or lower than the cutoff calibrator.
**COC = cocaine; BE = benzoylecgonine; CE = cocaethylene; NOR = norcocaine

2. Opioids in Hair: Solid-Phase Antigen Enzyme Immunoassay

Example Result for Opioids by Solid-Phase Analyte EIA

| Sample | Percent* | MS Results**, ng/10 mg hair | | | |
|---|---|---|---|---|---|
| | | Codeine | Morphine | MAM | Oxycodone |
| Negative (Bo) | 100 | | | | |
| Cutoff (2 ng/10 mg hair) | 43.9 | | | | |
| Positive Sample 59028 | 7.7 | 0.8 | 7.9 | 7.8 | 0.3 |
| Positive Sample 58641 | 13.3 | 3.6 | 48.8 | 85.4 | 0.8 |
| Positive Sample 58714 | 11.9 | 4.3 | 21.3 | 5.4 | 0 |
| Negative Sample 42621 | 92.8 | | | | |
| Negative Sample 42625 | 98.2 | | | | |
| Negative Sample 42644 | 93.6 | | | | |
| Minus 50% control | 66.3 | | | | |
| Plus 50% control | 28.9 | | | | |

**MAM = 6-monoacetylmorphine

3. Methamphetamine/MDMA in Hair: Solid-Phase Analyte Enzyme Immunoassay

Example Result for Methamphetamine/MDMA (Ecstasy) by Solid-Phase Analyte EIA

| Sample | Percent* | MS Results**, ng/10 mg hair | | | |
|---|---|---|---|---|---|
| | | METH | AMP | MDMA | MDA |
| Negative (Bo) | 100 | | | | |
| Cutoff (5 ng/10 mg hair) | 49 | | | | |
| Positive Sample 59708 | 11.3 | 2.6 | 0 | 214 | 6.7 |
| Positive Sample 59714 | 14.4 | 26.9 | 3.8 | 0 | 0 |
| Positive Sample 59718 | 47.2 | 6.7 | 0.7 | 0 | 0 |
| Negative Sample 42625 | 100.5 | | | | |
| Negative Sample 42642 | 102.2 | | | | |
| Negative Sample 42655 | 97.9 | | | | |

| Sample | Percent* | MS Results**, ng/10 mg hair | | | |
|---|---|---|---|---|---|
| | | METH | AMP | MDMA | MDA |
| Negative (Bo) | 100 | | | | |
| Minus 50% control | 67.2 | | | | |
| Plus 50% control | 39 | | | | |

**METH = methamphetamine; AMP = amphetamine; MDA = 3,4-methylenedioxyamphetamine; MDMA = 3,4-methylenedioxymethamphetamine

Example 2: Methanol Extraction of Analytes from Hair and Detection of Multiple Analytes Using Solid Phase Compositions Having Multiple Analytes Bound Thereto Hair samples were analyzed for the presence of multiple analytes (e.g., drugs of abuse) using methanolic extraction methods as disclosed in Yegles, et al., in: Analytical and Practical Aspects of Drug Testing in Hair, CRC Press, 2007, pp. 73-94; Jurado, C. in: Analytical and Practical Aspects of Drug Testing in Hair, CRC Press, 2007, pp. 95-125; Cheze, M. et al. in: Analytical and Practical Aspects of Drug Testing in Hair, CRC Press, 2007, pp. 163-185). Once extracted, the test samples were evaluated for the presence of multiple drug of abuse analytes using the methods and compositions disclosed herein, e.g., contacted with a solid phase having bound thereto two or more analytes and with one or more primary antibodies, each specific for a particular analyte; each primary antibody is then detected, e.g., through a label on the primary antibody or through detection of the primary antibody via a labeled secondary antibody.

I. Solutions

Acidified Methanol: Methanol with 1% HCl.

II. Treatment Procedure for Analyte Extraction for Enzyme Immunoassay

Two mL acidified Methanol was added to 10-12 mg hair in screw-cap glass tubes. Tubes were incubated at 60° C. overnight (16 hours). The methanol was removed into a clean tube and the hair dried by evaporation in a heat block at 50° C. Dried samples were reconstituted in PBS to a hair concentration of 10 mg hair/mL PBS.

III. Enzyme Immunoassay Using Multi-Analyte-Coated Microplates and Using Methanol Extracts of Hair: Cocaine, Opioids, Amphetamines FOR EIA, all reagents are filtered to avoid bacterial contamination.

A. Preparation of Microplates: Coating with BSA Analyte Conjugates—COMBO Plate

Microplates were prepared as described above in Example LIMA.

B. Analysis

The analysis of the extract was performed in the same manner as analysis of digest samples.

1. Cocaine in Hair: Solid-Phase Analyte Enzyme Immunoassay Using Methanol Extraction Example Result for Cocaine by Solid-Phase Analyte EIA

| Sample | Percent | Result | MS Results, ng/10 mg hair sample | | | |
|---|---|---|---|---|---|---|
| | | | COC | BE | CE | NOR |
| Negative (Bo) | 100 | | | | | |
| Cutoff (5 ng/10 mg hair) | 41.5 | | | | | |
| Positive Sample 60303 | 3.0 | POS | 174.1 | 14.5 | 20.9 | 2.5 |
| Positive Sample 60304 | 3.6 | POS | 118.7 | 33.5 | 0 | 2.3 |
| Positive Sample 60312 | 4.9 | POS | 70.5 | 26.8 | 0.2 | 2.3 |
| Positive Sample 60373 | 8.3 | POS | 26 | 6.1 | 2.3 | 0.4 |
| Negative Sample 42642 | 92.8 | | | | | |
| Negative Sample 42647 | 85.6 | | | | | |
| Negative Sample 42650 | 87.4 | | | | | |
| Negative Sample 42677 | 90.2 | | | | | |
| Negative Sample 42777 | 94.0 | | | | | |
| Minus 50% control (2.5 ng/10 mg hair) | 53.1 | | | | | |
| Plus 50% control (7.5 ng/10 mg hair) | 36.1 | POS | | | | |

2. Opioids in Hair: Solid-Phase Analyte Enzyme Immunoassay Using Methanol Extraction Example Result for Opioids by Solid-Phase Analyte EIA

| Sample | Percent | Result | MS Results, ng/10 mg hair sample | | | |
|---|---|---|---|---|---|---|
| | | | Codeine | Morphine | 6-MAM | Oxycodone |
| Negative (Bo) | 100 | | | | | |
| Cutoff (2 ng/10 mg hair) | 29.6 | | | | | |
| Positive Sample 60370 | 5.7 | POS | 0 | 10.5 | 38.9 | 71 |

-continued

| | Percent | Result | Codeine | Morphine | 6-MAM | Oxy-codone |
|---|---|---|---|---|---|---|
| Positive Sample 60575 | 27.3 | POS | 2.2 | 1.8 | 0 | 1 |
| Positive Sample 60482 | 16.4 | POS | 0.4 | 1.5 | 3.7 | 0 |
| Negative Sample 42642 | 108.8 | | | | | |
| Negative Sample 42647 | 105.7 | | | | | |
| Negative Sample 42650 | 88.9 | | | | | |
| Negative Sample 42677 | 105.7 | | | | | |
| Negative Sample 42777 | 112.1 | | | | | |
| Minus 50% control (2.5 ng/10 mg hair) | 47.7 | | | | | |
| Plus 50% control (7.5 ng/10 mg hair) | 20.1 | POS | | | | |

MS Results, ng/10 mg hair sample

3. Methamphetamine/MDMA in Hair: Solid-Phase Analyte Enzyme Immunoassay Using Methanol Extraction Example Result for Methamphetamine/MDMA (Ecstasy) by Solid-Phase Analyte EIA

| | Percent | Result | Meth | Amp | MDMA | MDA |
|---|---|---|---|---|---|---|
| Negative (Bo) | 100 | | | | | |
| Cutoff (5 ng/10 mg hair) | 46.7 | | | | | |
| Positive Sample 60320 | 25.4 | POS | 17.5 | 0.8 | | |
| Positive Sample 60360 | 12.9 | POS | 22.8 | 0.8 | 120 | 21 |
| Positive Sample 60435 | 25.4 | POS | 15 | 2.6 | | |
| Positive Sample 60448 | 20.3 | POS | 3.3 | 0.1 | 182.1 | 8.9 |
| Negative Sample 42642 | 92.2 | | | | | |
| Negative Sample 42647 | 94.1 | | | | | |
| Negative Sample 42650 | 94.1 | | | | | |
| Negative Sample 42677 | 95.7 | | | | | |
| Negative Sample 42777 | 95.3 | | | | | |
| Minus 50% control (2.5 ng/10 mg hair) | 54 | | | | | |
| Plus 50% control (7.5 ng/10 mg hair) | 41.4 | POS | | | | |

MS Results, ng/10 mg hair

OTHER EMBODIMENTS

A number of embodiments have been described. Nevertheless, it will be understood that various modifications may be made without departing from the spirit and scope of the disclosure provided herein. Accordingly, other embodiments are within the scope of the following claims.

What is claimed is:

1. A method for determining the amount of an analyte of interest in a sample, the method comprising contacting a solid phase composition with i) an antibody specific for the analyte of interest and ii) the sample under competitive binding conditions, and determining the amount of the analyte of interest in the sample;

wherein:
the solid phase composition comprises a polystyrene solid phase support and at least two different conjugates, wherein each conjugate comprises an albumin covalently conjugated to a drug of abuse or metabolite thereof selected from the group consisting of benzoylecgonine, an amphetamine, tramadol, PCP, morphine, oxycodone, methadone, cotinine, a benzodiazepine, buprenorphine, fentanyl, and a cannabinoid;
wherein the antibody specific for the analyte of interest binds to one of the at least two different conjugates;
the analyte is a drug of abuse or a metabolite thereof;
the at least two different conjugates are bound noncovalently or via adsorption to the polystyrene solid phase support;
the at least two different conjugates are randomly affixed as a mixture to a single solid phase component of the polystyrene solid phase support, wherein the polystyrene solid phase support comprises a plurality of single solid phase components, and each single solid phase component of the polystyrene solid phase support comprises the at least two different conjugates; and
the antibody specific for the analyte of interest is labeled or a labeled secondary antibody is introduced which is specific for the antibody specific for the analyte of interest.

2. The method of claim 1, wherein the antibody is detectably labeled.

3. The method of claim 2, wherein the antibody is detectably labeled with a fluorescent, luminescent, radioactive, or enzymatic label.

4. The method of claim 1, wherein the antibody is not labeled.

5. The method of claim 1, further comprising removing antibody that is not bound to the solid phase composition.

6. The method of claim 1, wherein the amount of the analyte is determined in the sample by comparing a signal generated by the antibody bound to the single solid phase component of the solid phase composition in the sample with a signal generated by the antibody bound to the single solid phase component of the solid phase composition in a control sample that does not comprise the analyte of interest.

7. The method of claim 6, wherein the antibody specific for the analyte of interest is labeled.

8. The method of claim 6, wherein the signal generated by the antibody bound to the single solid phase component of the solid phase composition is derived from a labeled secondary antibody which is specific for the antibody specific for the analyte of interest.

9. The method of claim 7 or 8, wherein the label is a fluorescent, luminescent, radioactive, or enzymatic label.

10. The method of claim 1, further comprising contacting the single solid phase component of the solid phase composition with a second antibody, where the second antibody is specific for the at least second different analyte bound to the single solid phase component, and determining the amount of the second analyte in the sample.

11. The method of claim 1, wherein the albumin is selected from HSA and BSA.

12. The method of claim 1, wherein the analyte of interest is selected from cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA).

13. The method of claim 1, wherein the sample is a bodily sample or a sample derived from a bodily sample.

14. The method of claim 13, wherein the bodily sample is from a human, and is selected from a tissue sample of the brain, heart, lung, kidney, liver, muscle, bone, stomach, intestines, and skin; a biological fluid selected from urine, blood, plasma, serum, saliva, semen, sputum, cerebral spinal fluid, mucus, sweat, vitreous liquid, and milk; and a keratinized structure.

15. The method of claim 14, wherein the bodily sample is a keratinized structure.

16. The method of claim 1, wherein the single solid phase component is a microwell of a microplate.

17. The method of claim 1, wherein the sample is derived from hair.

18. The method of claim 1, wherein the analyte of interest is selected from cocaine, PCP, an amphetamine, tramadol, a cannabinoid, morphine, oxycodone, methadone, fentanyl, cotinine, buprenorphine, and a benzodiazepine.

* * * * *